(12) United States Patent
Antoniou

(10) Patent No.: US 7,700,762 B2
(45) Date of Patent: Apr. 20, 2010

(54) PLASMID DNA CLARIFICATION

(75) Inventor: Chris Antoniou, Chelmsford, MA (US)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 10/875,673

(22) Filed: Jun. 23, 2004

(65) Prior Publication Data

US 2005/0112753 A1    May 26, 2005

(51) Int. Cl.
*C07H 1/06* (2006.01)
*C12P 19/34* (2006.01)

(52) U.S. Cl. ..................... 536/25.4; 435/91.1
(58) Field of Classification Search ........... None
See application file for complete search history.

(56) References Cited

U.S. PATENT DOCUMENTS

2002/0151048 A1 * 10/2002 Lander et al. ............ 435/320.1

FOREIGN PATENT DOCUMENTS

| WO | WO 93/11218 | 6/1993 |
|----|----|----|
| WO | WO 97/23601 | 7/1997 |
| WO | WO 00/05358 | 2/2000 |
| WO | WO 01/79486 | 10/2001 |

OTHER PUBLICATIONS

McNally, Mark T., "Rapid, Economical Filter Alternatiave to Chromosomal DNA Centrifugation in the Alkaline Lysis Plasmid Protocol", Biotechniques, 27(1), 68-71, Jul. 1, 1999.
Ruppert A., et al., "A Filtration Method for Plasmid Isolation Using Microtiter Filter Plates", Analytical Biochemistry, 230(1), 130-134 (Sep. 1, 1995).

* cited by examiner

*Primary Examiner*—Nancy Vogel

(57) ABSTRACT

A clarification system and method of using for plasmid DNA that is centrifugation-free. The system is comprised of a coarse filter, about 50 to about 200 microns pore size, followed by a prefilter of about 1 to about 2 micron pore size and then a final filter of about 0.22 micron. Preferably, the prefilter and final filter are combined into one filter housing to reduce system hold up volume and enhance recovery of the plasmid DNA. The method allows for continuous as well as batch operation.

6 Claims, 4 Drawing Sheets

PLASMID DNA CLARIFICATION

The present invention relates to a system and method of using the system to clarify plasmid DNA. More particularly, it relates to a normal flow filtration system and method of using the system to clarify plasmid DNA from cell lysate.

BACKGROUND OF THE INVENTION

Plasmid DNA is an important product for gene therapy applications. It is grown in host cells that are then lysed to release the plasmid DNA. The lysate is then clarified and the plasmid DNA is recovered using various regimes such as chromatography and the like.

Methods for clarifying lysate streams containing plasmid DNA have been described in WO 00/05358 and WO 97/23601. In both, the lysate is subjected to a centrifugation step that separates the plasmid DNA and smaller solids and particulates from the larger solids such as cell wall debris and the like. The supernatant containing the plasmid DNA is then carefully removed from the centrifuge and subjected to a series of filtration steps comprised of a coarse filter formed of a series of filter cloths (20 microns average pore size), followed by a prefiltration step (1-2 microns) and a final filtration step (about 0.2 microns).

Others have suggested using pad filters such as cellulosic fibers containing various fillers such as diatomaceous earth, clays, etc. or using a tangential flow filtration system (TFF) to clarify the lysate stream after centrifugation.

All of these systems are less than optimal for the recovery of plasmid DNA. Plasmid DNA typically accounts for less than 1%, more typically less than 0.5% by weight of the lysate stream, making the need for high recovery of the plasmid DNA important.

Centrifugation applies a shear to the constituents of the lysate stream which can damage the plasmid DNA. Additionally, recovery of the plasmid DNA containing portion of the stream is subjective and either is less than the total amount available or includes additional solids and particulates that adversely affect the downstream filtration steps (typically by prematurely clogging the filters.). Moreover, centrifugation requires an investment in capital equipment which is expensive, difficult to sanitize to FDA standards and requires the system be run in a batch format.

The proposed filtration train of the prior art has multiple steps and has a relatively low yield of plasmid DNA, typically less than about 80%. Under optimal laboratory conditions, these systems have yielded less than 90% of the available plasmid DNA. This is due to several factors. The selected filtration elements tend to interact with the plasmid DNA, binding some of it to their system. Additionally, each system has a minimum holdup volume that retains some of the plasmid DNA and never passes it on to the next stage of filtration.

Filter pads have not been an acceptable alternative as they irreversibly absorb a relatively high level of plasmid DNA, leading to low yields.

The use of TFF has been minimal as the TFF system with its constant washing of the plasmid DNA across the face of the membrane and its recirculation through one or more pumps applies a high shear on the plasmid DNA leading to reduced yields and reduced efficacy of the plasmid DNA that is recovered. Additionally, the yield of TFF devices is adversely affected by the high hold up volume of the TFF devices.

What is needed is a system and method of clarification that reduces the loss of yield and maintains the efficacy of the plasmid DNA recovered.

SUMMARY OF THE INVENTION

The present invention relates to a system that recovers at least 90% of plasmid DNA from a cell lysate stream. It uses a series of three filtration layers comprised of a coarse filter layer formed of a stainless steel sieve having a pore size of from about 50 to about 200 microns, a prefilter step formed of a filter having a pore size of from about 1 to about 2 microns, and a final filter step of a filter having a pore size of from about 0.1 to about 0.2 microns. It provides clarification with good plasmid DNA recovery without the use of centrifugation, allowing for a continuous process to be used.

Preferably the prefilter and final filter layers are part of a composite filter such that the stream first passes through the prefilter layer and then the final filter layer in one step.

IN THE DRAWINGS

DETAILED DESCRIPTION OF THE INVENTION

The present invention relates to a process for clarifying a plasmid DNA containing cell lysate stream without the need for centrifugation and with higher levels of plasmid DNA recovery.

Figure 1:
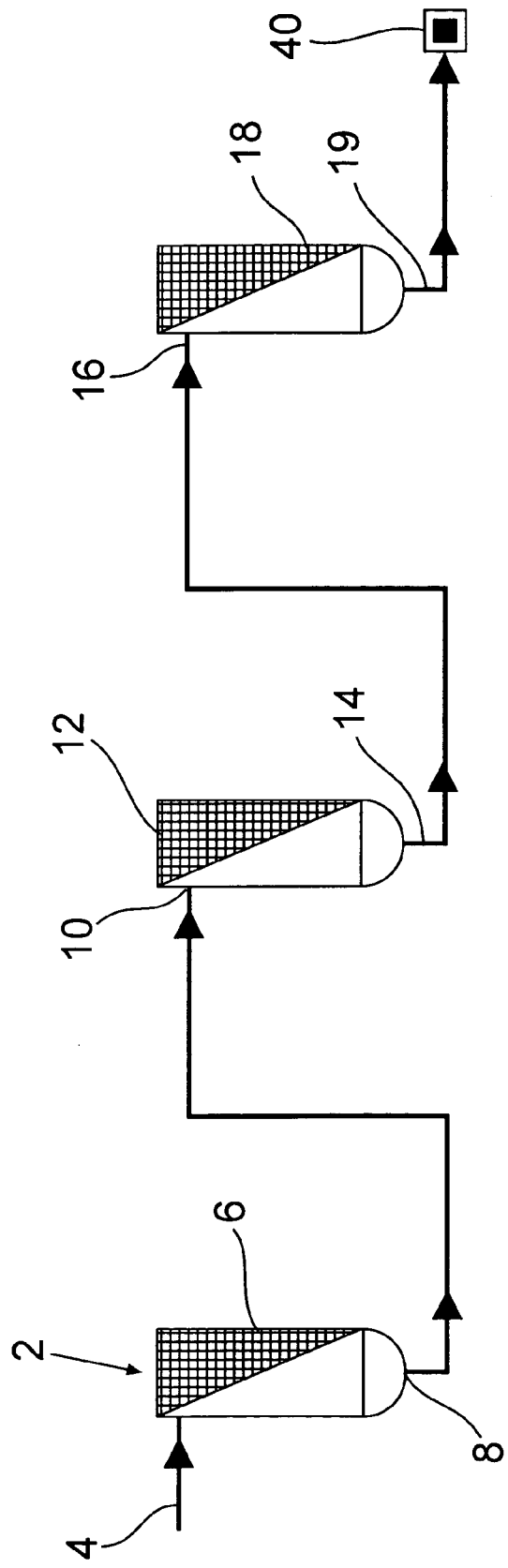
FIG. 1 shows a clarification system according to one embodiment of the present invention.

FIG. 1 shows a clarification system of the present invention. A cell lysate stream enters first filter stage 2 through an inlet pipe 4. The first filter stage is a coarse filter 6 comprised of a filter material having a pore size of from about 50 to about 200 microns. The outlet 8 from the coarse filter 6 is in fluid communication with the inlet 10 of a prefilter 12 formed of a normal flow filter having pore size of from about 1 to about 2 microns. The outlet 14 of the prefilter 12 is in fluid communication with the inlet 16 of the final filter 18 which has a pore size of about 0.22 micron. The outlet 19 of the final filter 18 is in fluid communication with the remainder of the processing equipment 40 that is used to purify the plasmid DNA via chromatography, viral removal, etc, A suitable coarse filter is a stainless steel sieve having a pore size from about 50 microns to about 200 microns, preferably from about 50 to about 100 microns, more preferably about 80 microns. One such filter is made by Cole-Parmer of Vernon Hills, Ill. (part no A029595-16). Other coarse filters having the same pore size range may be made from other metals such as nickel, titanium, palladium, copper, aluminum and the like or glass, ceramic or sintered plastic. It is desirable for the filter to be as few layers as possible, preferably two or less layers of material, more preferably a single layer, so as to minimize the loss of the plasmid DNA in the filter and reduce the holdup volume of the system.

A suitable prefilter layer maybe made of a depth filter, or a combination depth filter/sheet filter such as the POLYSEP™ II filter available from Millipore Corporation of Billerica, Mass. The POLYSEP™ II filter is formed of a borosilicate glass depth filter that is followed by a mixed cellulose ester sheet membrane layer downstream of the glass layer. A preferred device is one that uses the 1.0 micron nominal pore size glass filter followed by a 1.2 micron nominal pore size mixed ester membrane. Other prefilters may also be used and can be made from materials selected from the group consisting of polyethylene, polypropylene, borosilicate glass, mixed cellulose esters, and combinations thereof. The filter media may be in the form of a depth filter, such as a mat of fibers, spun bounded fibers, non-woven fabrics or woven fabrics or in the form of a membrane sheet or in a combination of the two layers as discussed above. A preferred prefilter has a pore size of between about 1 and about 3 microns, preferably about 1 to about 2 microns, more preferably about 1.2 microns.

A suitable final filter is formed of material selected from the group consisting of PVDF, such as the DURAPORE® membrane available from Millipore Corporation of Billerica, Mass., polyethersulfone, such as the EXPRESS® or EXPRESS® PLUS membrane available from Millipore Corporation of Billerica, Mass., polysulfone, polyarylsulphones, polyphenylsulphones, polyamides, and the like. Preferably, the selected filter is hydrophilic, either inherently due to the polymer selected or by application of a coating, a grafting, including a hydrophilic polymer such as poly vinyl pyrilidone (PVP) or other methods well known to one of ordinary skill in the art in membrane manufacture.

Figure 2:
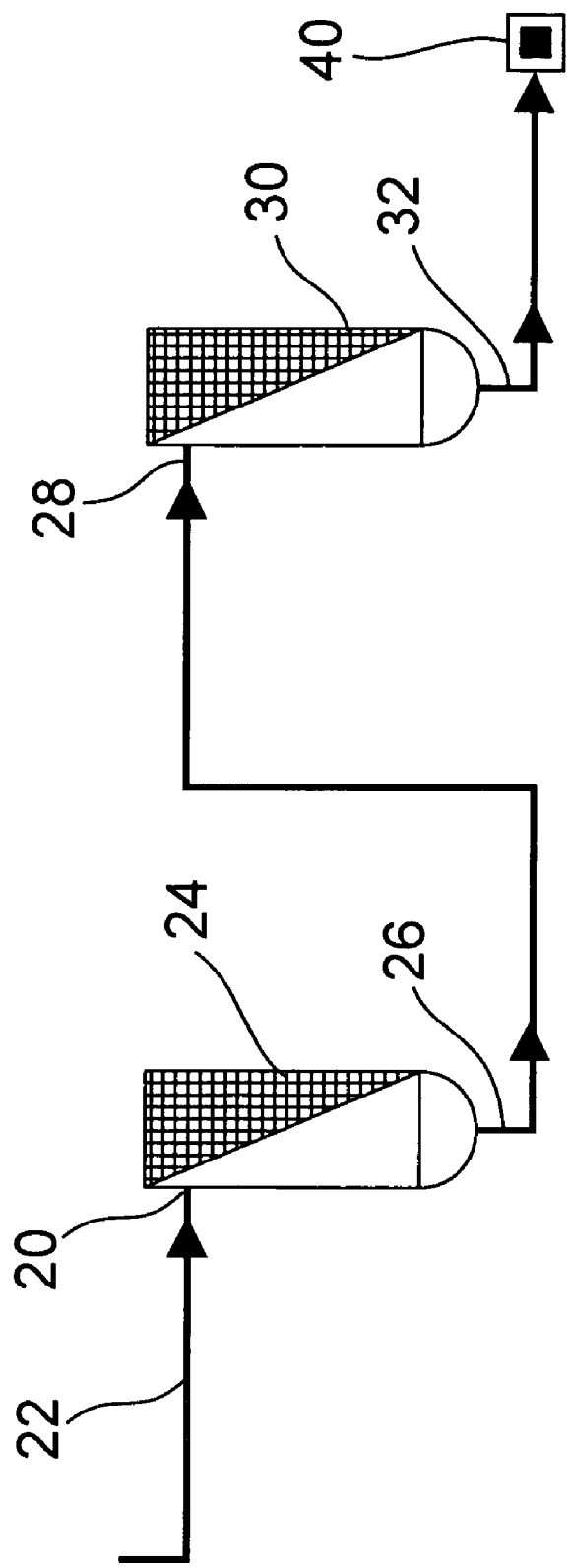
FIG. 2 shows a second embodiment of the present invention.

FIG. 2 shows a second embodiment of a clarification system of the present invention. A cell lysate stream enters first filter stage 20 through an inlet pipe 22. The first filter stage is a coarse filter 24 such as a stainless steel filter material having a pore size of from about 50 to about 200 microns. The outlet 26 from the coarse filter 24 is in fluid communication with the inlet 28 of a combination prefilter/final filter device 30 formed of a normal flow filter having one or more layers of prefilter material of pore size of from about 1 to about 2 microns and one or more layers downstream of the first set of layers that is a final filter which has a pore size of about 0.22 micron. The outlet 32 of the combination prefilter/final filter 30 is in fluid communication with the remainder of the processing equipment 40 that is used to purify the plasmid DNA via chromatography, viral removal, etc, This embodiment of FIG. 2 is a preferred embodiment in that it combines two filtration steps into one thereby eliminating the loss of fluid due to hold up volume in one rather than two filtration steps. This helps to increase the yield of the plasmid DNA.

A suitable combination prefilter/final filter is known as the OPTICAP™ Multimedia filter available from Millipore Corporation of Billerica, Mass. It is a dual layer filter in a disposable cartridge configuration. The first layer is a 1.2 micron mixed cellulosic ester layer and the final layer is a 0.2 hydrophilic PVDF membrane. Fluid containing the plasmid DNA passes into the cartridge, through the prefilter layer and then through the final filter layer yielding a solid-free plasmid DNA containing stream. Other combinations of filter layers may be used to form other multimedia layer filters in the present invention if desired so long as they provide good clarification and high plasmid DNA yields.

EXAMPLE 1

A cell lysate stream containing plasmid DNA was processed through a system as shown and described in FIG. 2 using a 80 micron stainless steel coarse filter made by Cole-Parmer of Vernon Hills, Ill. (part no A029595-16) followed by an OPTICAP™ Multimedia filter (a 1.2 micron nominal pore size mixed cellulose ester membrane followed by a 0.22 micron DURAPORE® PVDF membrane) available from Millipore Corporation of Billerica, Mass.

Figure 3:
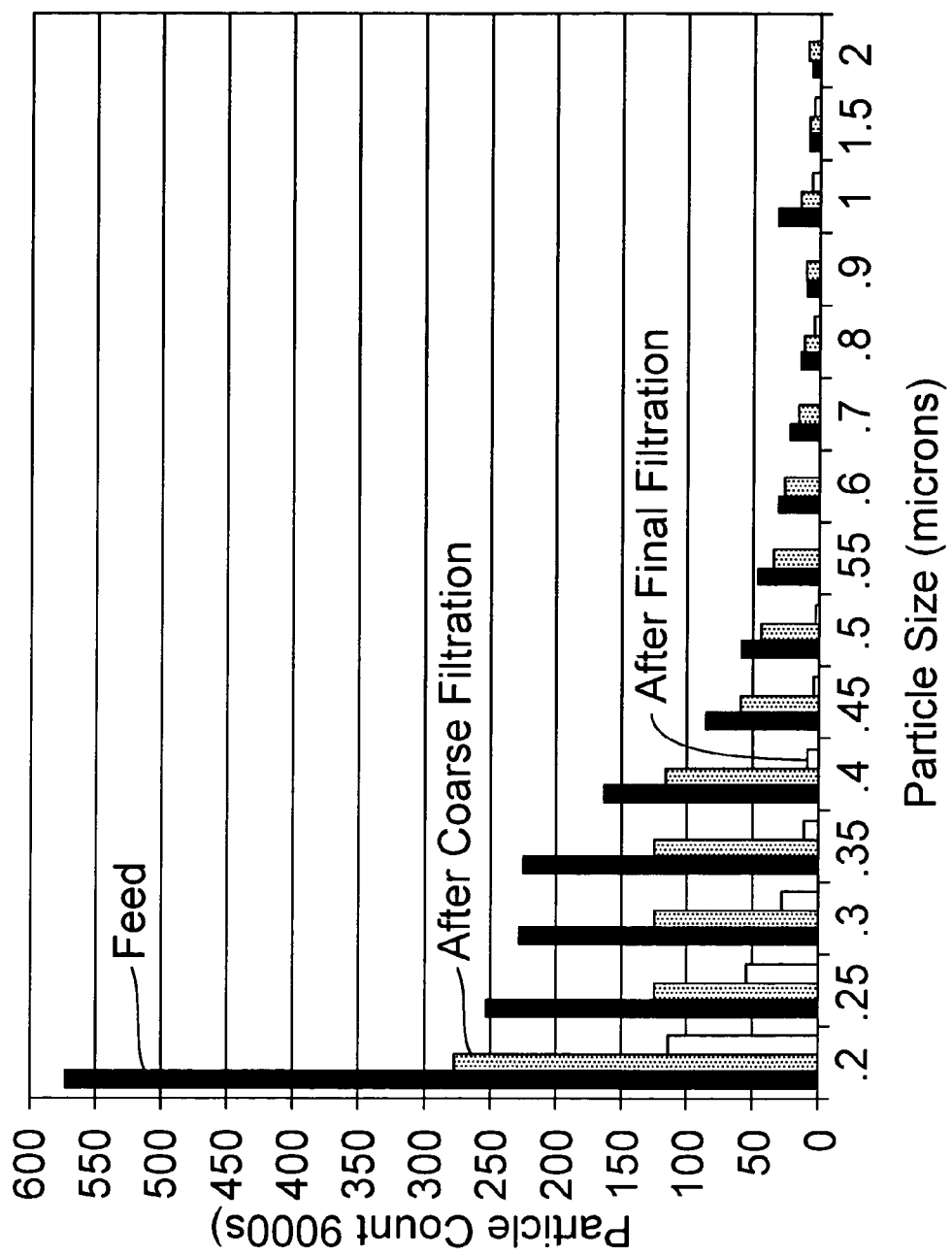
FIG. 3 shows a graph of the relative size and amount of particulates found in a cell lysate stream before and after the various steps of the present invention.

The particle size and amount of particles of that size stream was analyzed before processing, after the coarse filtration and after the combination prefilter/final filter step. FIG. 3 shows a graph of the particles up to two microns in size that were dejected in the stream during analysis. As can be clearly seen, the system according to the invention clarified the stream significantly.

EXAMPLE 2

A cell lysate stream containing plasmid DNA was processed through a system as shown and described in FIG. 1 using a 80 micron stainless steel coarse filter made by Cole-Parmer of Vernon Hills, Ill. (part no A029595-16) followed by a POLYSEP™ II filter (1.0 micron nominal pore size glass filter followed by a 1.2 micron nominal pore size mixed ester membrane) available from Millipore Corporation of Billerica, Mass. followed by a final filter (a 0.22 micron DURAPORE® hydrophilic PVDF membrane in cartridge format) available from Millipore Corporation of Billerica, Mass.

A cell lysate stream containing plasmid DNA was processed through a system as shown and described in FIG. 2 using a 80 micron stainless steel coarse filter made by Cole-Parmer of Vernon Hills, Ill. (part no A029595-16) followed by an OPTICAP™ Multimedia filter (a 1.2 micron nominal pore size mixed cellulose ester membrane followed by a 0.22 micron DURAPORE® PVDF membrane) available from Millipore Corporation of Billerica, Mass.

Figure 4:
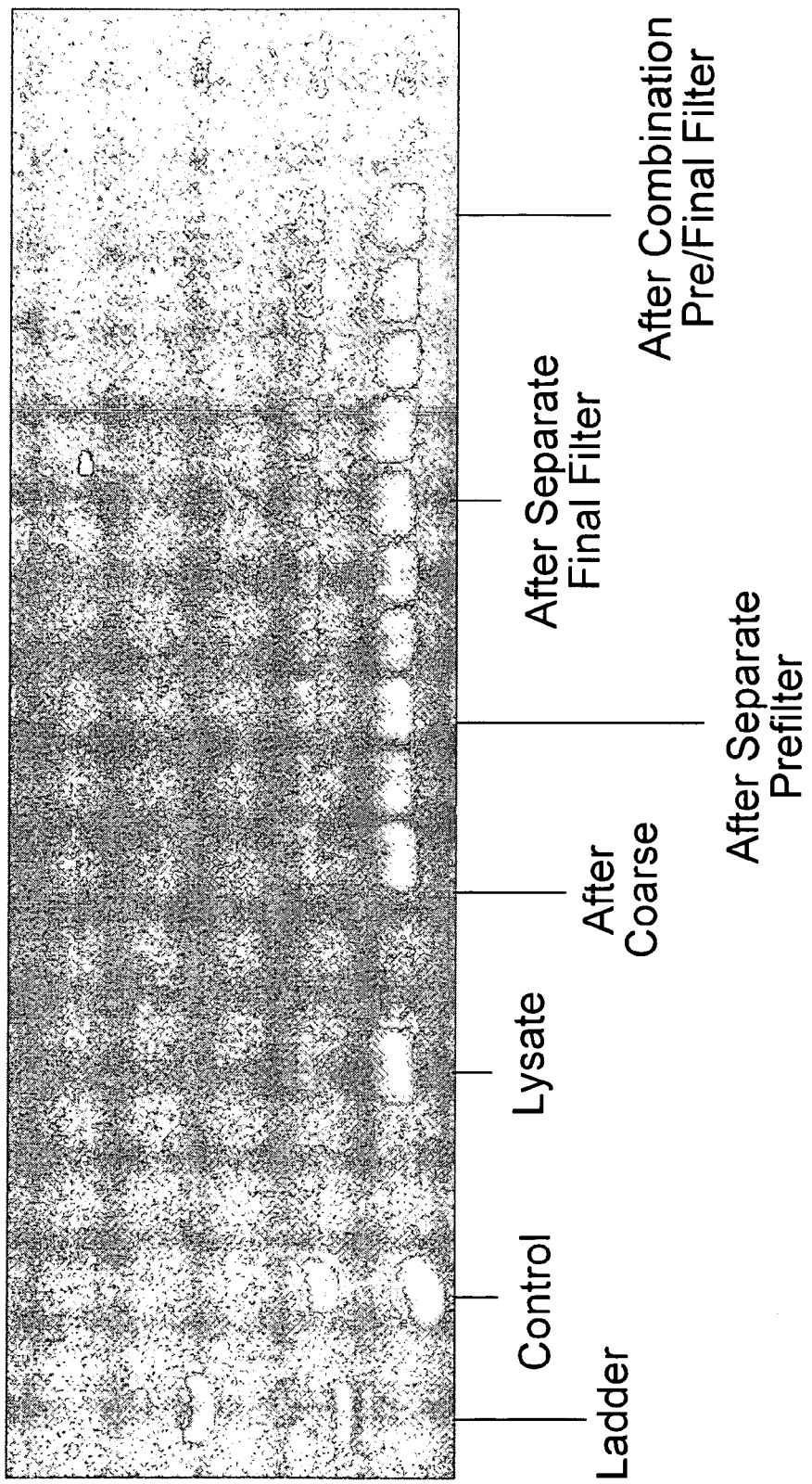
FIG. 4 shows a gel analysis of plasmid recovery by the methods and systems of eth present invention.

The plasmid DNA yield was determined by gel analysis as shown in FIG. 4. As can be seen the plasmid recovered from the filtration systems of the present invention was relatively high and exceeded 90% in each case (as determined by calculation from the gel analysis).

The present invention provides a system having high capacity, maximum positive change in the turbidity of the fluid processed (evidencing high solids removal), small particle count and minimal plasmid DNA yield loss, all without the need for a centrifugation step. It allows one to reduce system holdup volume by eliminating processing steps (increasing potential yield) and to run the system and process as a continuous rather than batch formatted process.

What I claim:

1. A process for the clarification of plasmid DNA comprising the steps of providing a cell lysate stream containing plasmid DNA, subjecting the stream to a first filtration step comprised of a coarse filter formed of a stainless steel sieve having a pore size of from 50 to 200 microns to form a first permeate stream, subjecting the first permeate stream to a second filtration step comprised of a prefilter layer having a pore size of from about 1 to about 2 microns to form a second permeate stream, and subjecting the second permeate stream to a final filtration step comprised of about a 0.22 micron filter to create a third permeate stream and recovering the plasmid DNA from the third permeate stream wherein the recovery is at least 90% of the plasmid present in the cell lysate stream.

2. A system for the clarification of a cell lysate stream containing plasmid DNA comprising an inlet for the lysate stream to enter the system, the inlet connected to a coarse filter formed of a stainless steel sieve having a pore size of from about 50 to about 200 microns, an outlet from the coarse filter in fluid communication with an inlet of a prefilter, the prefilter having a pore size of from about 1 to about 2 microns, an outlet from the prefilter in fluid communication with an inlet of a final filter formed of filter having about a 0.22 micron pore size and an outlet from the final filter for a permeate stream and recovering at least 90% of the the plasmid DNA present in the cell lysate stream from the permeate stream.

3. A process for the clarification of a cell lysate stream containing plasmid DNA comprising applying the lysate stream to an inlet of a coarse filter formed of a stainless steel sieve having a pore size of from about 50 to about 200 microns, flowing the stream through the coarse filter to an outlet from the coarse filter in fluid communication with an inlet of a prefilter having a filter having a pore size of from about 1 to about 2 microns, flowing the stream through the prefilter to an outlet from the prefilter in fluid communication with an inlet of a final filter formed of filter having about a 0.22 micron pore size, flowing the stream through the final filter to an outlet from the final filter for a permeate stream and recovering at least 90% of the the plasmid DNA present in the cell lysate stream from the permeate stream.

4. A plasmid clarification system comprising an inlet pipe for carrying a cell lysate stream to a first filtration stage, the first filtration stage being a metal sieve having a pore size of from about 50 to about 200 microns, an outlet from the coarse filter in fluid communication with an inlet of a prefilter/final filter device formed of a normal flow filter having one or more layers of prefilter material of a pore size of from about 1 to about 2 microns and one or more layers of a final filter material downstream of the one or more layers of prefilter material, the final filter material having a pore size of about 0.22 micron and an outlet from the prefilter/final filter device for a permeate stream, recovering the plasmid DNA in the permeate stream, the outlet from the prefilter/final filter device being in fluid communication with the remainder of the processing equipment used to purify the plasmid DNA, recovering at least 90% of the plasmid DNA present in the cell lysate stream in the permeate stream and supplying the permeate stream containing the plasmid DNA to the remainder of the processing equipment to purify the plasmid DNA.

5. The system of claim 2 wherein the prefilter and final filters are combined in a composite filter having a first prefilter layer followed by a final filter layer.

6. The process of claim 3 wherein the prefilter and final filter steps are combined in a composite filter having a first prefilter layer followed by a final filter layer.

* * * * *